US006556296B1

(12) United States Patent
Palo

(10) Patent No.: US 6,556,296 B1
(45) Date of Patent: Apr. 29, 2003

(54) METHOD FOR CHARACTERIZING SAMPLES BY DETERMINATION OF A FUNCTION OF AT LEAST ONE SPECIFIC PROPERTY OF PARTICLES IN A SAMPLE

(75) Inventor: Kaupo Palo, Harju maakond (EE)

(73) Assignee: Evotec BioSystems AG, Hamburg (DE)

( * ) Notice: Subject to any disclaimer, the term of this patent is extended or adjusted under 35 U.S.C. 154(b) by 0 days.

(21) Appl. No.: 09/509,491

(22) PCT Filed: Sep. 29, 1998

(86) PCT No.: PCT/EP98/06165

§ 371 (c)(1),
(2), (4) Date: Jun. 12, 2000

(87) PCT Pub. No.: WO99/17086

PCT Pub. Date: Apr. 8, 1999

Related U.S. Application Data

(60) Provisional application No. 60/060,344, filed on Sep. 29, 1997.

(30) Foreign Application Priority Data

Mar. 21, 1998 (EP) .............................. 98105160

(51) Int. Cl.[7] ............................. G01N 21/64; G01J 3/30
(52) U.S. Cl. .................... 356/317; 356/338; 250/458.1; 250/459.1
(58) Field of Search ................. 356/317, 318, 356/338, 417; 435/6; 250/458.1, 459.1

(56) References Cited

U.S. PATENT DOCUMENTS 6,049,380 A * 4/2000 Goodwin et al. ........... 356/317
6,376,843 B1 * 4/2002 Palo ........................ 250/458.1
6,388,746 B1 * 5/2002 Eriksson et al. ............ 356/318

OTHER PUBLICATIONS

Keller et al., Single–Molecule Fluorescence Analysis in Solution, Applied Spectroscopy, vol. 50, No. 7, Jul. 1996 pp. 12A–32A.
Madrazo et al., Time–Interval Statistics Applied to the Analysis of Low–Polydispersity Samples for Low Light–Intensity Levels, Applied Optics, vol. 33, No. 21, Jul. 1994, pp. 4899–4905.

* cited by examiner

Primary Examiner—Frank G. Font
Assistant Examiner—Layla Lauchman
(74) Attorney, Agent, or Firm—Jacobson Holman PLLC

(57) ABSTRACT

A method for characterizing samples having fluorescent particles, by monitoring fluctuating intensities of radiation emitted by said particles in at least one measurement volume, the monitoring being performed by at least one detection means, said method comprising the steps of:

Figure 1:
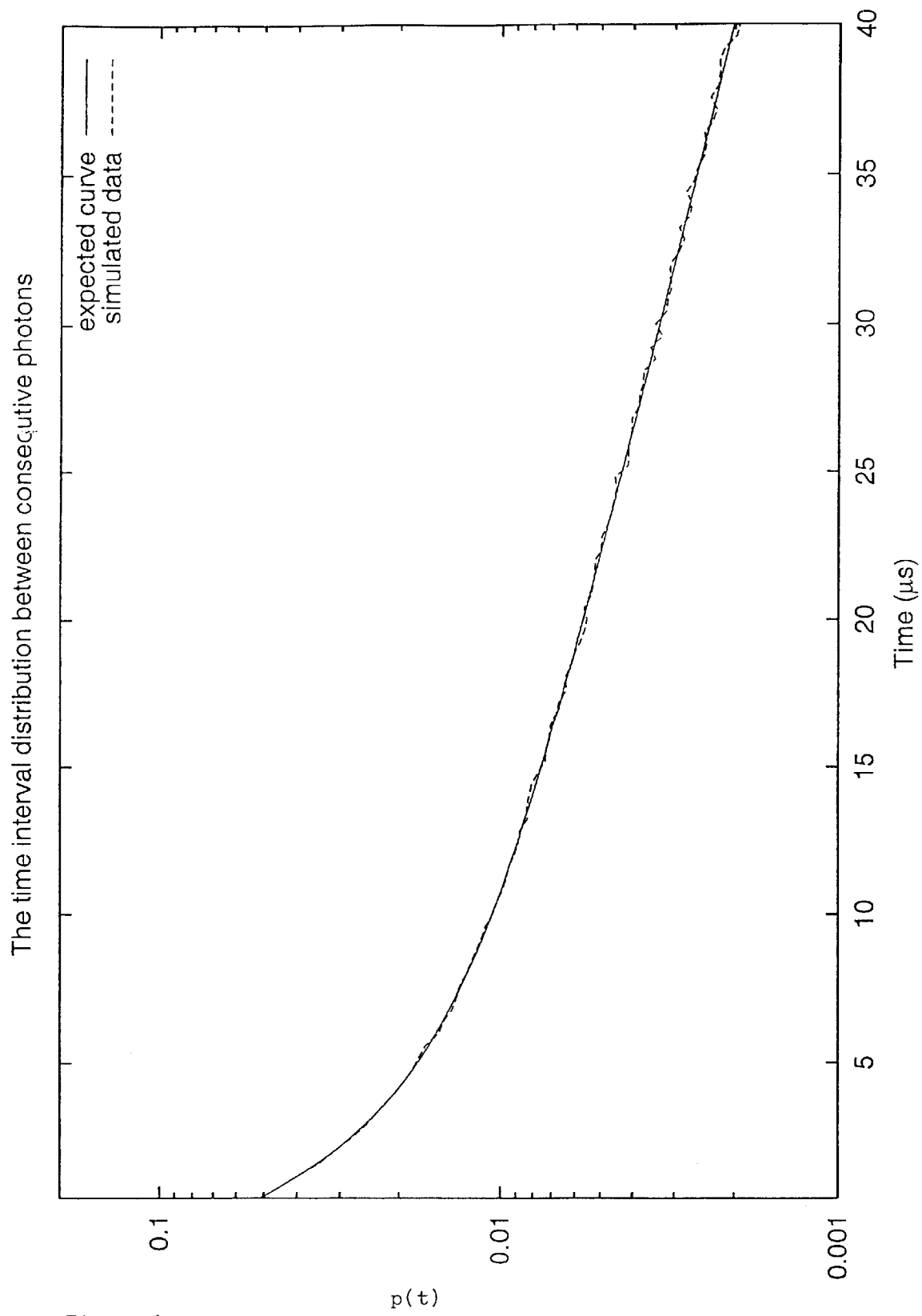

a) measuring in a repetitive mode a length of time intervals between photon counts,
b) determining a function or a series of functions of the length of said time intervals,
c) determining a function of at least one specific physical property of said particles on basis of said function or said series of functions of the length of time intervals, by finding a close fit between the experimentally determined and a theoretical function or series of functions of the length of said time intervals, the latter of which takes into account parameters of the spatial brightness function characteristic for the optical set-up.

24 Claims, 2 Drawing Sheets

METHOD FOR CHARACTERIZING SAMPLES BY DETERMINATION OF A FUNCTION OF AT LEAST ONE SPECIFIC PROPERTY OF PARTICLES IN A SAMPLE

This application is a 371 of PCT/EP98/06165, filed Sep. 29, 1998, which claims benefit of U.S. Provisional Application No. 60/060,344 filed Sep. 29, 1997.

The present invention relates to a method for characterizing samples by determination of a function of at least one specific physical property of units of said sample.

The essence of a number of pharmacological, biological and chemical problems is to detect substances in a sample or to measure the interaction or reaction of these substances. In order to measure the substances in a sample more specifically, usually at least one of the reactants is radioactively or luminescently labelled. A convenient and sensitive type of labels are fluorescent labels.

Widely used methods to monitor interactions by fluorescence are the determination of changes in overall fluorescence intensity or in anisotropy of fluorescence. However, a number of side effects, such as surface binding or fluorescence from impurities, often lead to interpretation problems and artifacts. A second reason which has induced interest towards refined methods of analysis is the need to work with small amounts of a large number of samples in the field of high throughput screening and large capacity diagnostics.

New opportunities for assay development were opened when the technology for monitoring fluorescence from single fluorophore molecules became available. The first successful studies on fluorescence intensity fluctuations were performed by Magde, Elson and Webb (Biopolymers, Vol. 13, 29-61, 1974) who demonstrated the possibility to detect number fluctuations of fluorescent molecules and established a research field called fluorescence correlation spectroscopy (FCS). FCS was primarily developed as a method for determining chemical kinetic constants and diffusion coefficients. The experiment consists essentially in measuring the variation of the number of molecules of specific reactants in time in a defined open volume of solution. Microscopic fluctuations of the concentration of the reactant are detected as fluorescence intensity fluctuations from a small, open measurement volume. The measurement volume is defined by a focussed laser beam, which excites the fluorescence, and a pinhole in the image plane of the microscope collecting fluorescence. Intensity of fluorescence emission fluctuates in proportion with the changes in the number of fluorescent molecules as they diffuse into and out of the measurement volume and as they are created or eliminated by the chemical reactions. Technically, the direct outcome of an FCS experiment is the calculated autocorrelation function of the measured fluorescence intensity.

An important application of FCS is to determine concentrations of fluorescent species having different diffusion rates in a mixture. In order to separate the two terms corresponding to translational diffusion of two kinds of particles in the autocorrelation function of the fluorescence intensity, at least about a two-fold difference in diffusion time is needed, which corresponds generally to an eight-fold difference in the mass of the particles. Furthermore, if one succeeds in separating the two terms in the autocorrelation function of fluorescence intensity, it is yet not sufficient for determining the corresponding concentrations except if one knows the relative brightness of the two different types of particles.

Possible biophysical applications further demand the ability to analyze complex mixtures of different species. For that purpose, Palmer and Thompson studied higher order correlation functions of fluorescence intensity fluctuations and have outlined methods for determining the number densities and relative molecular brightness of fluorescence of different fluorescent species (Biophys. J., Vol. 52, 257-270, August 1987). Their technique may in principle proof useful in detecting and characterizing aggregates of fluorescently labelled biological molecules such as cell surface receptors, but has a major disadvantage of being rather complex, so that data processing of an experiment including the calculation of high-order correlation functions last hours.

A considerably less complicated method than calculation of high order auto-correlation functions for characterizing mixtures of fluorescent species of different specific brightness is a calculation of higher order moments of fluorescence intensity out of experimentally determined distribution of the number of photon counts. This method was presented by Qian and Elson (Biophys. J., Vol. 57, 375-380, February 1990; Proc. Natl. Acad. Sci. USA, Vol. 87, 5479-5483, July 1990). The method of moments, however, is hardly suitable for characterizing complex samples or selecting between competing models of the sample or checking whether the given model is appropriate.

Further improvements were made according to the disclosure of WO-A-98/16814. This publication describes a method for analyzing samples by measuring numbers of photon counts per defined time interval in a repetitive mode from light emitted, scattered and/or reflected by particles in said sample, and determining the distribution of the number of photon counts per said time intervals, characterized in that the distribution of specific brightness of said particles is determined from said distribution of the number of photon counts. The method can also be applied to study fluorescent samples. This special embodiment is the so called fluorescence intensity distribution analysis (FIDA). While FCS distinguishes between different species according to their diffusion time, FIDA distinguishes between them according to their specific brightness.

Kask et al. describe possibilities for the use of fluorescence correlation spectroscopy in the nanosecond time range (Eur. Biophys. J., 12: 163-166, 1985). However, there is no discussion on determining a distribution of a specific physical property from the measured photon interval distribution function in their report.

Keller et al. (Applied Spectroscopy, vol. 50, no. 7, p. 12A–32A, 1996) disclose methods for single-molecule fluorescence analysis in solution.

Madrazo et al. (Applied Optics, vol. 33, no. 21, p. 4899–4905, 1994) disclose a time-interval-statistics method that is based on the measurement of the Laplace transform of the probability function of the time intervals between two successive photoelectrons. This method has been applied to experiments of light diffusion from low-polydispersity samples from which the scattered intensity is weak.

An object of the invention is to provide a reliable and fast method for characterizing samples.

The object of the present invention is solved with the method having the features of claim 1.

It is to be understood that the following description is intended to be illustrative and not restrictive. Many embodiments will be apparent to those of skill in the art upon reviewing the following description. By way of example, the invention will be described primarily with reference to monitoring numbers of photon counts from light emitted by fluorescently labelled particles in a sample. This is because fluorescence is a very sensitive means allowing to monitor single molecules, and still rather selective allowing to distinguish between different species. However, in some embodiments it may be desirable to monitor numbers of photon counts of other origin than fluorescence.

The term "unit of a sample" refers, in general, to subparts of the sample which are capable of emitting, scattering and/or reflecting radiation. A sample might contain a number of identical units or different units which preferably can be grouped into species. The term "different species" refers also to different states, in particular different conformational states, of a unit such as a molecule. Fluorescently labelled or naturally fluorescent molecules, molecular complexes, vesicles, cells, beads and other particles in water or other liquids are examples of fluorescent units in liquid samples, while examples of fluorescent units or particles of a solid sample are impurity molecules, atoms or ions, or other fluorescence centers.

What is meant by the term "specific physical property" is generally a physical measurable property having a certain value or interval of values for one species and, in general, another value or interval of values for another species if said species have been characterized on basis of said specific physical property. Examples of specific physical properties are: diffusion coefficient, absorption cross-section, quantum yield of fluorescence, specific brightness, anisotropy of fluorescence, fluorescence decay time, ratio of fluorescence intensity passing through different optical filters, etc.

The specific brightness in the sense of the present invention is a physical characteristic which expresses in what extent a unit of given species is able to emit, scatter and/or reflect radiation. It is thought to characterize single units and therefore the value of specific brightness is neither depending on concentration of the units, nor on the presence of other units. Thus, a change of the total count rate of photons emitted, scattered and/or reflected from the measurement volume, if only due to a change in concentration of the total number of units, does not influence the value of specific brightness. Specific brightness of a unit is usually expressed in terms of the mean count rate per unit which is a weighted average of the count rate over coordinates of the unit in the measurement volume. In some cases, one might prefer to express the specific brightness in count rates corresponding to a unit positioned in a place where the count rate has its top values. This could e.g. be the center of the focus of an incident beam.

According to the invention, a very rapid and reliable characterization of samples having units which emit, scatter and/or reflect radiation is possible. In a first step, the length of time intervals between photon counts is measured in a repetitive mode. In a second step, a function or a series of functions of the length of said time intervals is determined. In a third step, a function of at least one specific physical property of said units is determined on basis of said function or said series of functions of the length of time intervals. The latter determination is preferably performed by finding a close fit between the experimentally determined and a theoretical function or series of functions of the length of said time intervals. It is preferred that the latter takes into account parameters of the spatial brightness function characteristic for the optical set-up which is to be used within experiments.

The spatial brightness function might e.g. be accounted for in analysis in the following way. Theoretical expressions of the photon interval distribution (corresponding either to consecutive photon counts or to photon counts with a certain number of intermediate photon counts) contain integrals over spatial coordinates of functions of spatial brightness function. For example, the cumulative distribution function of time intervals between consecutive counts looks as follows:

$$P(\tau) = 1 - \frac{1}{\Omega}\exp\left\{\sum_i C_i \int_V [\exp(-Q_i B(x)\tau) - 1] dV\right\}$$

$$\sum_i C_i Q_i \int_V B(x)\exp(-Q_i B(x)\tau) dV.$$

where $$\Omega = \sum_i C_i Q_i \int_V B(x) dV.$$

with
  $P(\tau)$ : cumulative distribution function of $\tau$
  $\tau$: time interval between two consecutive photon counts
  $C_i$: concentration of i-th species
  V: volume
  $Q_i$: specific brightness of i-th species
  $B(x)$: brightness as a function of spatial coordinates In real situations, the spatial brightness function $B(x)$ often has a rather complicated form and its determination would be extremely inconvenient. According to the invention, this difficulty has been overcome by replacing the integration over spatial coordinates by integration over volume elements of given brightness. Even though the volume-brightness distribution is initially unknown for a given equipment, it has turned out to be possible to determine it empirically, with a sufficient accuracy for time interval distribution analysis (see example below).

What characteristics of the spatial brightness function can be employed when determining the expected/theoretical function or series of functions of the length of time intervals are values of volumes of the sections of the measurement volume corresponding to a selected set of values of the spatial brightness. Typically, a set of twenty or thirty values of the spatial brightness positioned at a constant distance from each other in the logarithmic scale have been selected, covering two or three orders of magnitude. Contributions from the lower brightness areas can be accounted for by a single parameter, their relative contribution to fluorescence intensity. Intensity fluctuations of this light can be neglected. Because of the large number of the sections of the measurement volume, it would be less preferred to consider volumes corresponding to each of the sections as independent variables. It is convenient to consider them as variables depending on a few other parameters, and determine the values of these parameters which yield a close fit between the experimentally determined and the calculated distribution of the length of time intervals. Conveniently, a relatively simple model of the optical set-up is applied, which is not accounting for aberrations of the optics used, and which determines volumes of the sections of the measurement volume. For instance, the volumes of the sections depend on values of the convergence angle of the laser beam and the diameter of the pinhole. It might therefore be preferred to use the pinhole dimensions and the convergence angle of the incident laser beam as modelling parameters of the spatial brightness function.

Alternatively, simple mathematical expressions with formal parameters can be used instead of physical models for determining the volumes of spatial sections. The values of the formal parameters should preferably be selected in such a way that a close fit between experimental and theoretical functions of the length of time intervals is achieved. Formal flexible expressions are advantageous because they yield a good fit between experimental and theoretical functions of the length of time intervals. Secondly, calculations based on simple mathematical expressions are very fast compared to those based on physical models.

In a preferred embodiment, the length of time intervals between consecutive photon counts are measured in a repetitive mode.

It might also be preferred to measure the length of time intervals between photon counts separated by a given number of intermediate photon counts. A series of functions might be built by measuring time intervals between photon counts separated by different numbers of intermediate photon counts. In such a series, one might e.g. measure the length of time intervals between consecutive photon counts, between photon counts separated by one intermediate photon count, between photon counts separated by two intermediate photon counts, etc.

In a further preferred embodiment, said function of at least one specific physical property of said units and/or said function of the length of said time intervals is a distribution function.

It might be preferred to monitor the fluctuating intensities of radiation emitted, scattered and/or reflected by said units in at least one measurement volume with the help of only one detection means. If one is interested in characterization of species according to more than one specific physical property, for example, to different polarizations or spectral sensitivities of fluorescence detection, then it might be preferred to use more than one detection means. In a further embodiment, a plurality of assays might be performed simultaneously, requiring a parallelization of detection means. Any detector which is capable to detect radiation emitted, scattered and/or reflected by units of the sample may be used. Appropriate detection means such as an avalanche photodiode, a photo-multiplier or conventional photodiodes are well known to those of skill in the art. It can also be preferred to use a multidetector consisting of a monolithic configuration of a plurality of detectors, especially if one wants to measure a set of samples in parallel as it is the case in miniaturized high throughput screening. It can further be preferred to use a two-dimensional multiarray detector.

According to a preferred embodiment, the units or particles are molecules, aggregates, vesicles, cells, viruses, bacteria, centers, or mixtures thereof in solids, liquids or gases. It may be preferred to group units into species which can be distinguished by at least one of their specific physical properties. At least one of the species can be luminescent, preferably fluorescent, and/or can be luminescently labelled.

In one preferred embodiment, the specific physical property characterizing said units is the specific brightness.

It may further be preferred to characterize fluorescent units by the polarization ratio of their fluorescence, or fluorescence anisotropy, or any other property expressing the extent of polarization of fluorescence.

In one embodiment, the specific physical property characterizing the fluorescent units is the ratio of fluorescence intensities corresponding to different excitation wavelengths. and/or different spectral sensitivities of fluorescence detection, or any other property expressing the dependence of fluorescence intensity on the wavelength of excitation and/or detection.

In a further preferred embodiment, the specific physical property characterizing said fluorescent units is lifetime of fluorescence.

It can further be preferred to characterize said units by their diffusion coefficient, or correlation time of radiation intensity fluctuations, or any other property directly related to said diffusion coefficient.

The specific physical properties, in particular luminescence properties like fluorescence lifetime or fluorescence anisotropy, of the units can be varied by conjugating them with a specific luminophore via different linker molecules. It may be preferred to use polymeric linker molecules consisting of a varying number of equal or different monomers.

The luminescence properties of the units may also be varied by conjugating them with a first molecule, as e.g. biotin, which binds a luminescently labelled second molecule, as e.g. luminescently labelled avidin or streptavidin.

The luminescence properties of a particle can also be changed by energy transfer. Energy absorbed by a donor is transferred upon close contact to a luminophor of an acceptor and subsequently emitted.

In a preferred embodiment, the measurement volume is only a part of the total volume of the sample and said units are diffusing and/or being actively transported into and out of said measurement volume and/or said sample is actively transported and/or optically scanned. If said units, e.g. fluorescent particles, are sufficiently small, then diffusion is fast enough for data acquisition from a great number of counting intervals. However, if the characteristic time of diffusion is substantially longer than the time interval for measuring fluorescence intensity, then active transport (flow or scanning) can considerably save time of data acquisition.

The method according to the present invention is particularly well suited for high throughput screening, diagnostic purposes, monitoring polymerization, aggregation or degradation processes, or for general analytical purposes, such as environmental analytics or process control.

In screening procedures, substances that are possibly pharmacologically active can be analyzed through their interaction with specific receptors by examining said interaction with binding of a luminescently labelled ligand to receptors wherein natural receptors on their carrier cells as well as receptors on receptor-overexpressing carrier cells or receptors on vesicles or receptors in the form of expressed molecules or molecular complexes may be used. Moreover, the interaction of substances with enzymes in solution or in their genuine cellular environment can be detected by monitoring a change of the substrate of the enzyme, e.g. a change in size, brightness, rotational diffusion, or any other of the above mentioned fluorescence properties. Another means of determining enzyme activity is to add a fluorescently labelled molecule, which binds to either educt or product of the enzymatic reaction. Another method for investigating pharmacological activity of substances is the measurement of reporter systems such as Green Fluorescent Protein (GFP) expression, and of the properties of molecules to which GFP is attached. Further applications, especially concerning the performance of assays, are disclosed in WO-A-94/16313 which is hereby incorporated by reference.

For the detection of specific recognition reactions, potential active substances can be present in complex natural, synthetic or semisynthetic mixtures which are subjected to separation prior to analysis. These mixtures can be separated first e.g. by chromatography to test the individual fractions for the presence of functional compounds preferably "on line" in a capillary at the end of a separation matrix. The coupling of fractionating methods with FCS detection is described in detail in WO-A-94/16313.

Often, aggregation and degradation are phenomena to be monitored. Aggregates display e.g. brightnesses and diffusion times different from the monomers. In determining both properties, the measurements become more precise.

In sequencing according to the method of Sanger, oligomers of different length, of which the terminating nucleic acid is labelled with a dye, are identified. Advanced techniques, as e.g. the one described in DE-A-38 07 975 (incorporated by reference), use dyes which exhibit different properties, such as fluorescence lifetime, according to the type of base they are attached to. The determination of a base is much more safe if several properties, such as fluorescence life-time and brightness, or any other specific physical property, are determined according to the invention and cross checked for consistency. In a preferred embodiment, the sample to be sequenced is separated by gel or capillary electrophoresis, or a separation step is conducted by capillary electrochromatography, electrohydrodynamic migration or related electrokinetic methods.

In one embodiment, said function of the length of time intervals is fitted using a priori information on said sample. In a further embodiment, said function of the length of time intervals is processed by applying an inverse transformation with linear regularization (ITR) or inverse-trans-formation with constraints (ITC) or inverse transformation with regularization and constraints (ITRC). Inverse transformation can be used to determine which composition of the sample would yield the theoretical values of the function of the length of time intervals close to the experimental data. Because of statistical errors and limited sizes of measured data, inverse transformation is often an ill-posed mathematical problem, characterized by wild oscillations in its outcome. ITR, ITC and ITCR stabilize the mathematical problem by looking for a "regular" (e.g. a smooth) or constrained solution, for example by minimizing the sum of squared deviations of statistical data and a function of the solution itself, penalizing "irregular", usually irreproducible structures in the outcome, or values having no physical meaning. An example of constraining is disallowing negative values for concentrations (For the method of ITR, see, e.g., W. H. Press, S. A. Teukolsky, W. T. Vetterling, B. P. Flannery, Numerical recipes in C: the art of scientific computing, second edition, Cambridge University Press, 1992, p. 808, which is hereby incorporated by reference).

In fluorescence studies, it may be advantageous to take measures for reducing the background count rate, arising from Raman scattering in the solute material and dark count rate of the detector, with respect to the count rate per unit. In particular, it is in some cases preferred to use measurement volumes smaller than $10^{-12}$ l, more preferably smaller than $10^{-14}$ l.

The measurement volumes or samples can preferably be arranged on two-dimensional carriers, such as membranes or sheets having wells. Suitable carrier systems are e.g. described in WO-A-94/16313. In a further preferred embodiment, said measurement volumes can be arranged in a linear way, as e.g. in a capillary Advantageously, the high signal to background count rate and the small optical measurement volume may be achieved by using at least one microscope objective, preferably with a numerical aperture $\geq 0.9$, in a confocal manner for both focussing the incident laser beam and collecting radiation emitted, scattered and/or reflected by units in said sample.

A suitable device is disclosed in WO-A-94/16313 which is hereby incorporated by reference.

In a further preferred embodiment, the measurement volume is restricted by the use of elements of near field optical microscopy. Near field optical microscopy means here that the light passes through an aperture with at least one of its dimensions being smaller than the wavelength of the light used and which is in direct contact to the measurement volume. The aperture may consist of an opaque layer with at least one hole of said diameter or at least one slit of appropriate width and/or a tapered glass fiber or wave guide with a tip diameter of said width, optionally coated with an opaque layer outside. Near field optical microscopy can be used for focussing the excitation light of the units, and/or collecting the light emitted by the units. A suitable device is disclosed in WO-A-96/13744 which is hereby incorporated by reference.

Another preferred embodiment combines near field optical microscopy for the excitation light path, and conventional optical microscopy for the emission light path, or vice versa. The present invention profits from such a realization in the sense that the size of the measurement volume is reduced compared to conventional confocal microscopy. Thus, the present invention can be used to measure higher concentration of particles as with other optical schemes.

In a preferred embodiment of the method, multiple photon excitation is used to excite a unit. Multiple photon excitation means that the sum, difference or any other combination of wave frequencies of two, three or more photons is used for excitation of e.g. luminescence. Such an excitation scheme has an advantage in a sense that the excitation probability is not linearly dependent on excitation intensity, but on the second or higher power. Thus, the multiple photon excitation is mostly limited to the volume of the laser focus, whereas outside the laser focus no spurious excitation is generated. The present invention profits from such an excitation scheme. in a sense that less background is generated compared to single photon excitation, and that no pinhole is necessary to restrict the measurement volume. Appropriate laser sources of picosecond or subpicosecond pulses are well known to those of skill in the art.

EXAMPLE 1

The way how the distribution of specific brightnesses of fluorescent molecules is determined from experimental time interval distribution is illustrated by this example. Data to be analyzed in this example are computer simulated. This computing method saves much time because it does not require the preparation of many different experimental situations. However, brightnesses of molecules have been selected to correspond to fluorescent molecules in aqueous solutions. When data were simulated, as well as in fitting the data, the uneven spatial brightness distribution characteristic to real equipments was accounted with the help of N=30 volume elements corresponding to 30 different values of spatial brightness. The following formula. were used for calculating the spatial brightnesses ($B_j$) and sizes ($V_j$) of the volume elements:

$$B_i = \frac{N-i}{N}$$

$$V_i = a_0(i+1) + a_1(i+1)^2 + a_2(i+1)^3 + a_3\delta i+1, N)$$

$$i=0,\ldots,N-1$$

In simulations it is not necessary to use realistic values of parameters of spatial brightness function. Nevertheless, numeric multipliers on the right side of the last expression In simulations it is not necessary to use realistic values of parameters of spatial brightness function. Nevertheless, numeric multipliers on the right side of the last expression are selected at values of the corresponding parameters of the spatial brightness function independently determined for the laser-excited fluorescence microscope (ConfoCor®, Carl Zeiss Jena GmbH, Jena & EVOTEC BioSystems AG, Hamburg) to be used in experiments (in arbitrary units):

$$a_0 = 4.6 \times 10^{-3}$$

$$a_1 = 7.4 \times 10^{-4}$$

$$a_2 = 5.1 \times 10^{-5}$$

$$a_3 = 1.4$$

A time interval distribution was simulated for a solution of single fluorescent species at C=0.75 particles per measurement volume and Q=150 kHz per particle. The data were simulated with a time resolution of 0.4 $\mu$s, and 100 data points were involved, covering the range of 0 to 40 $\mu$s. In curve fitting, at least one of the volume parameters or concentration was fixed because of the arbitrariness of the volume unit. We fixed $a_0$. From fitting, the following values of parameters were determined:

C=0.734 particles per measurement volume

Q=145.2 kHz per particle $$a_1 = 7.35 \times 10^{-4}$$

$$a_2 = 5.21 \times 10^{-5}$$

$$a_3 = 1.8 \times 10^{-4}$$

EXAMPLE 2

Figure 2:
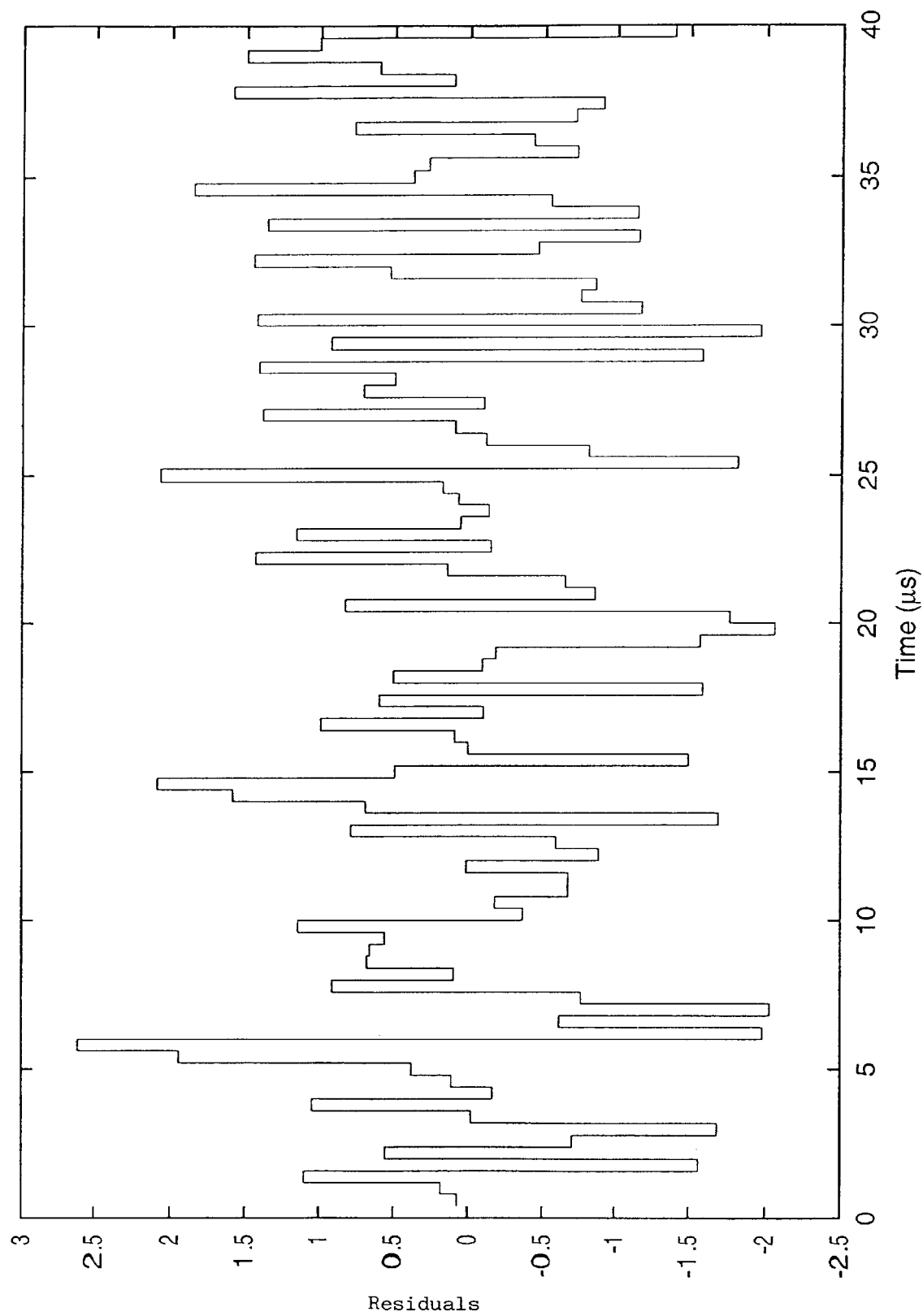

Another simulated time interval distribution function corresponding to a solution of two fluorescent species, with specific brightnesses of 1000 kHz/particle and 5 kHz/particle, and concentrations of 0.01 particles per measurement volume and 7.0 particles per measurement volume, is presented on FIG. 1, together with its fit curve. FIG. 2 shows the residuals. The simulated curve corresponds to an experiment of 10 s duration. In curve fitting, the values of spatial parameters were fixed. Curve fitting yielded the following values of parameters:

$$C_1 = 0.00978(\pm 2.8\%) \text{ particles per measurement volume}$$

$$Q_1 = 1011.8(\pm 1.5\%) \text{ kHz per particle}$$

$$C_2 = 7.011(\pm 19\%) \text{ particles per measurement volume}$$

$$Q_2 = 5.009(\pm 19\%) \text{ kHz per particle}$$

What is claimed is:

1. A method for characterizing samples having fluorescent particles, by monitoring fluctuating intensities of radiation emitted by said particles in at least one measurement volume, the monitoring being performed by at least one detection means, said method comprising the steps of:
   a) measuring in a repetitive mode a length of time intervals between photon counts
   b) determining a function or a series of functions of the length of said time intervals,
   c) determining a function of at least one specific physical property of said particles based on the determined function or series of functions of the length of time intervals, by finding a close fit between the determined function or series of functions of the length of time intervals and a theoretical function or series of functions of the length of said time intervals, the latter of which takes into account parameters of a spatial brightness function.

2. The method according to claim 1, wherein said length of time intervals is measured between consecutive photon counts.

3. The method according to claim 1, wherein said length of time intervals is measured between two photon counts separated by a given number of intermediate photon counts.

4. The method according to claim 1, wherein said series of functions is built by measuring time intervals between two photon counts separated by different numbers of intermediate photon counts.

5. The method according to claim 1, wherein said function of at least one specific physical property of said particles and/or said function of the length of said time intervals is a distribution function.

6. The method according to claim 1, wherein said particles are molecules, aggregates vesicles, cells, viruses, bacteria, beads, or mixtures thereof in liquids or gases.

7. The method according to claim 1, wherein said particles can be grouped into species which can be distinguished by the at least one of their specific physical properties.

8. The method according to claim 1, wherein the specific physical property characterizing said particles is specific brightness.

9. The method according to claim 1, wherein the specific physical property characterizing said particles is the polarization ratio of their fluorescence, or fluorescence anisotropy, or any other property expressing the extent of polarization of fluorescence.

10. The method according to claim 1, wherein the specific physical property characterizing said particles is the ratio of fluorescence intensities corresponding to different excitation wavelengths and/or different spectral sensitivities of fluorescence detection, or any other property expressing the dependence of fluorescence intensity on the wavelength of excitation and/or detection.

11. The method according to claim 1, wherein the specific physical property characterizing said particles is lifetime of fluorescence.

12. The method according to claim 1, wherein the specific physical property characterizing said particles is the diffusion coefficient, or correlation time of radiation intensity fluctuations, or any other property directly related to said diffusion coefficient.

13. The method according to claim 1, wherein the fluorescence properties of particles are varied by conjugating them with a first molecule, in particular biotin, which binds a fluorescently labeled second molecule, in particular fluorescently labeled avidin or streptavidin.

14. The method according to claim 1, wherein the fluorescence properties of a particle are changed by energy transfer, in which energy absorbed by said particle is transferred upon close contact to a fluorophore of an acceptor and subsequently emitted.

15. The method according to claim 1, wherein said particles each carry a number of binding sites for fluorescent particles.

16. The method according to claim 1, wherein the measurement volume is only a part of the total volume of said sample and has a volume $\leq 10^{-12}$ 1, preferably $\leq 10^{14}$ 1.

17. The method according to claim 1, wherein said particles are diffusing and/or being actively transported into and out of said measurement volume and/or said sample is actively transported and/or optically scanned.

18. The method according to claim 1, wherein the measurement volumes or samples are arranged on a two-dimensional carrier, in particular on a membrane or in sheets having wells, or in linear way, preferably in a capillary system.

19. The method according to claim 1, wherein a confocal microscope set-up is used, comprising at least one microscope objective, preferably with a numerical aperture $\geq 0.9$, for both focusing an incident laser beam and collecting radiation emitted by said particles of said sample, a dichroic mirror, a pin-hole in the image plane of said microscope objective, a detection means, a data acquisition means, and optionally means for scanning and/or actively transporting said sample.

20. The method according to claim 1, wherein said measurement volume is restricted by the use of elements of near field optical microscopy, or their combination with conventional microscopy.

21. The method according to claim 1, wherein fluorescence is induced using multiple photon excitation.

22. The method according to claim 1, wherein said distribution of the length of time intervals is fitted using a priori information on said sample.

23. The method according to claim 1, wherein said distribution of the length of time intervals is processed by applying an inverse transformation with linear regularization and/or constraints.

24. The method according to claim 1, for use in high throughput screening, diagnostics, monitoring polymerization, aggregation and degradation processes, particle sorting, or nucleic acid sequencing.

* * * * *